US012559460B2

(12) United States Patent
Nomura et al.

(10) Patent No.: US 12,559,460 B2

(45) Date of Patent: Feb. 24, 2026

(54) METHOD FOR PRODUCING AROMATIC HETEROCYCLIC RING-SUBSTITUTED DIFLUOROACETIC ACID DERIVATIVE

(71) Applicant: AGC Inc., Tokyo (JP)

(72) Inventors: Yoshitaka Nomura, Tokyo (JP); Eiichiro Anraku, Tokyo (JP)

(73) Assignee: AGC Inc., Tokyo (JP)

(*) Notice: Subject to any disclaimer, the term of this patent is extended or adjusted under 35 U.S.C. 154(b) by 551 days.

(21) Appl. No.: 17/813,499

(22) Filed: Jul. 19, 2022

(65) Prior Publication Data

US 2022/0380311 A1 Dec. 1, 2022

Related U.S. Application Data

(63) Continuation of application No. PCT/JP2021/003822, filed on Feb. 3, 2021.

(30) Foreign Application Priority Data

Feb. 6, 2020 (JP) ................................ 2020-019211

(51) Int. Cl.

| | |
|---|---|
| ***C07D 213/26*** | (2006.01) |
| ***C07D 205/10*** | (2006.01) |
| ***C07D 213/24*** | (2006.01) |
| ***C07D 215/16*** | (2006.01) |
| ***C07D 233/26*** | (2006.01) |
| ***C07D 237/30*** | (2006.01) |
| ***C07D 241/44*** | (2006.01) |
| ***C07D 277/64*** | (2006.01) |

(52) U.S. Cl.

CPC ......... *C07D 213/24* (2013.01); *C07D 205/10* (2013.01); *C07D 215/16* (2013.01); *C07D 237/30* (2013.01); *C07D 241/44* (2013.01); *C07D 277/64* (2013.01)

(58) Field of Classification Search

CPC .. C07D 213/26; C07D 215/16; C07D 233/26; C07D 237/30; C07D 241/44; C07D 277/64

See application file for complete search history.

(56) References Cited

U.S. PATENT DOCUMENTS

2015/0087836 A1 3/2015 Yoshizawa et al.

FOREIGN PATENT DOCUMENTS

| | | |
|---|---|---|
| JP | 2012-167047 A | 9/2012 |
| JP | 2015-514676 A | 5/2015 |

OTHER PUBLICATIONS

International Search Report issued Mar. 16, 2021 in PCT/JP2021/003822, filed on Feb. 3, 2021, 3 pages.

Loska et al., "New Synthesis of 2-Heteroarylperfluoropropionic Acids Derivatives by Reaction of Azine N-Oxides with Hexafluoropropene", Chem. Eur. J., vol. 14, 2008, 13 Pages.

Loska et al., "Synthesis of Alkyl Aryl(heteroaryl)acetates from N-Oxides, 1,1-Difluorostyrenes, and Alcohols" Organic Letters, vol. 15, No. 22, 2013, 4 Pages.

Ma et al., "Dual Role of Ethyl Bromodifluoroacetate in the Formation of Fluorine-Containing Heteroaromatic Compounds", Chem Commun., Royal Society of Chemistry, vol. 54, No. 65, 2018, 5 Pages.

Loska et al., "Simple Method for the Introduction of Tetra fluoroethyl Substituents into Nitrogen Heterocycles", Mendeleev Commun., vol. 16, No. 3, 2006, 3 Pages.

Mailey et al., "Fluoroalkyl pyridines. A Novel Rearrangement", The Journal of Organic Chemistry, vol. 33, No. 8, Aug. 1968, 2 Pages.

*Primary Examiner* — Bruck Kifle

(74) *Attorney, Agent, or Firm* — Oblon, McClelland, Maier & Neustadt, L.L.P.

(57) ABSTRACT

A method for producing an aromatic heterocycle-substituted difluoroacetic acid derivative having a partial structure represented by the formula (III), by reacting an N-oxido aromatic heterocyclic compound having a partial structure represented by the formula (I) with tetrafluoroethylene in the presence of a compound represented by the formula (II): R—YH, in a solvent selected from an aromatic hydrocarbon solvent, an ester solvent and an ether solvent:

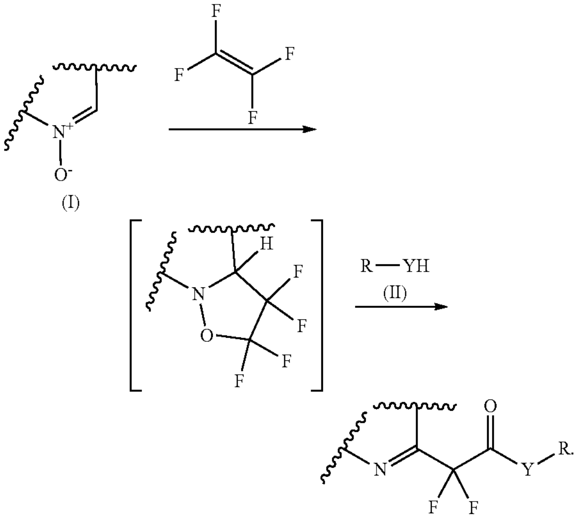

(I)

(III)

20 Claims, No Drawings

METHOD FOR PRODUCING AROMATIC HETEROCYCLIC RING-SUBSTITUTED DIFLUOROACETIC ACID DERIVATIVE

CROSS REFERENCE TO RELATED APPLICATIONS

This application is a continuation application of PCT/JP2021/003822, filed on Feb. 3, 2021, and claims priority to Japanese Patent Application No. 2020-019211, filed on Feb. 6, 2020, the entire contents of which are incorporated herein by reference.

TECHNICAL FIELD

The present invention relates to a method for producing aromatic heterocycle-substituted difluoroacetic acid derivatives.

BACKGROUND ART

Aromatic heterocycle-substituted difluoroacetic acid derivatives are useful as synthetic intermediates for pharmaceutical or agrochemical products.

As methods for producing aromatic heterocycle-substituted fluoroalkyl carboxylic acid derivatives, for example, Non-Patent Document 1 discloses the following methods:

a method of reacting various aromatic heterocycle N-oxides with hexafluoropropene ($CF_2{=}CFCF_3$) and methanol in N,N-dimethylformamide to produce methyl 2-(2-heteroaryl) perfluoropropionate in two steps (Scheme 5, Table 2), a method of reacting various aromatic heterocycle N-oxides with hexafluoropropene ($CF_2{=}CFCF_3$) and an amine in N,N-dimethylformamide to produce 2-(2-heteroaryl)perfluoropropionamide in two steps (Scheme 12, 13), and a method of reacting quinoline N-oxide with chlorotrifluoroethylene ($CF_2{=}CFCl$) and methanol in N,N-dimethylformamide at 100° C. to produce methyl 2-chloro-2-fluoro-2-(2-quinolyl)acetate (Scheme 17).

4

However, none of the documents describe productions of aromatic heterocycle-substituted difluoroacetic acid derivatives or reactions with tetrafluoroethylene ($CF_2{=}CF_2$).

DOCUMENT LIST

Non-Patent Document

Non-Patent Document 1: Chem. Eur. J. 2008, vol. 14, pp 2577-2589

SUMMARY OF THE INVENTION

Problems to be Solved by the Invention

6

The aim of the present invention is to provide a method capable of easily and inexpensively producing aromatic heterocycle-substituted difluoroacetic acid derivatives.

Means of Solving the Problems

7

The present inventors have conducted intensive studies in an attempt to solve the above-mentioned problems and found that by reacting an N-oxido aromatic heterocyclic compound having a partial structure represented by the following formula (I) with tetrafluoroethylene in the presence of a compound represented by the following formula (II) in a specific solvent, an aromatic heterocycle-substituted difluoroacetic acid derivative having a partial structure represented by the following formula (III) with few by-products can be easily and inexpensively produced in one step, which resulted in the completion of the present invention.

8

Accordingly, the present invention provides the following.

[1] A method for producing an aromatic heterocycle-substituted difluoroacetic acid derivative having a partial structure represented by the formula (III):

9

(III)

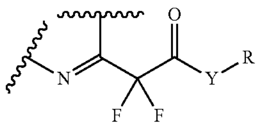

10 wherein

R is a $C_{1-8}$ alkyl group, a $C_{3-8}$ cycloalkyl group, a $C_{7-16}$ aralkyl group or a $C_{6-10}$ aryl group, wherein the $C_{1-8}$ alkyl group is optionally substituted by substituent(s) selected from a halogen atom, a cyano group, a $C_{1-6}$ alkoxy group and a $C_{1-6}$ haloalkoxy group, and the $C_{3-8}$ cycloalkyl group, $C_{7-16}$ aralkyl group and $C_{6-10}$ aryl group are each optionally substituted by substituent(s) selected from a halogen atom, a cyano group, a $C_{1-6}$ alkyl group, a $C_{1-6}$ haloalkyl group, a $C_{1-6}$ alkoxy group and a $C_{1-6}$ haloalkoxy group, Y is O, S or $NR^Y$, and $R^Y$ is a hydrogen atom or a $C_{1-8}$ alkyl group, or $R^Y$ and R are optionally taken together to form a nitrogen-containing heterocycle with the nitrogen atom to which they are bond (hereinafter, to be referred to as aromatic heterocycle-substituted difluoroacetic acid derivative (III)), which comprises reacting an N-oxido aromatic heterocyclic compound having a partial structure represented by the formula (I):

11

(I)

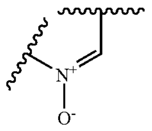

12

(hereinafter, to be referred to as N-oxido aromatic heterocyclic compound (I)) with tetrafluoroethylene, in the presence of a compound represented by the formula (II): R—YH wherein each symbol in the formula is as defined above (hereinafter, to be referred to as compound (II)), in a solvent selected from an aromatic hydrocarbon solvent, an ester solvent and an ether solvent.

[2] The method according to the above [1], wherein the reaction is carried out at temperature in the range of 100 to 300° C.

[3] The method according to the above [1] or [2], wherein the reaction is carried out under pressure in the range of 0.1 to 10.0 MPa.

[4] The method according to any of the above [1] to [3], wherein the N-oxido aromatic heterocyclic compound having the partial structure represented by the formula (I) is an N-oxido aromatic heterocyclic compound represented by the formula (IA) or (IB):

13

(IA)

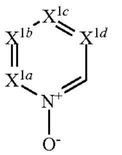

(IB)

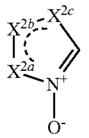

14 wherein $X^{1a}$ is $CR^{1a}$ or N;

$X^{1b}$ is $CR^{1b}$ or N;

$X^{1c}$ is $CR^{1c}$ or N;

$X^{1d}$ is $CR^{1d}$ or N;

$R^{1a}$, $R^{1b}$, $R^{1c}$ and $R^{1d}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{1a}$ and $R^{1b}$, $R^{1b}$ and $R^{1c}$, or $R^{1c}$ and $R^{1d}$ are optionally taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group;

$X^{2a}$ is $CR^{2a}$, N, $NR^{2a}$, S or O;

$X^{2b}$ is $CR^{2b}$ or N;

$X^{2c}$ is $OR^2$c, N, $NR^{2c}$, S or O; and $R^{2a}$, $R^{2b}$ and $R^{2c}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{2a}$ and $R^{2b}$, or $R^{2b}$ and $R^{2c}$ are optionally taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group (hereinafter, to be referred to as N-oxido aromatic heterocyclic compound (IA) or (IB)).

[5] The method according to the above [4], wherein the N-oxido aromatic heterocyclic compound having the partial structure represented by the formula (I) is represented by the formula (IA), and $R^{1a}$ and $R^{1b}$, $R^{1b}$ and $R^{1c}$, or $R^{1c}$ and $R^{1d}$ in the formula are taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

[6] The method according to the above [4], wherein the N-oxido aromatic heterocyclic compound having the partial structure represented by the formula (I) is represented by the formula (IA), and $R^{1a}$, $R^{1b}$, $R^{1c}$ and $R^{1d}$ in the formula are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group.

[7] The method according to the above [4], wherein the N-oxido aromatic heterocyclic compound having the partial structure represented by the formula (I) is represented by the formula (IB), and $R^e$a and $R^{2b}$, or $R^{2b}$ and $R^{2c}$ in the formula are taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

[8] The method according to the above [4], wherein the N-oxido aromatic heterocyclic compound having the partial structure represented by the formula (I) is represented by the formula (IB), and $R^{2a}$, $R^{2b}$ and $R^{2c}$ in the formula are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group.

Effect of the Invention

15

According to the present invention, by an easy and inexpensive method of flowing tetrafluoroethylene into N-oxido aromatic heterocyclic compound (I) in the presence of compound (II) in a specific solvent, aromatic heterocycle-substituted difluoroacetic acid derivative (III) with few by-products can be produced in one step.

DESCRIPTION OF EMBODIMENTS

16

Hereinafter, the definitions of the groups used herein will be described in detail. Unless otherwise specified, the groups have the following definitions.

17

As used herein, the compound represented by the formula is indicated by adding the formula number to the "Compound". For example, the compound represented by the formula (1) is indicated as "Compound (1)".

As used herein, the numerical range represented by "to" or "-" means a numerical range in which the numbers before and after "to" or "-" are the lower and upper limits.

As used herein, when the name of arbitrary group is given the element symbol "C" and a numerical range by numbers before and after "-", it means that the group has an integer number of carbon atoms whose the lower and upper limits are the numbers before and after the "-". For example, an alkyl group having 1 to 3 carbon atoms may be referred to as a "$C_{1-3}$ alkyl group", which indicates each of —$CH_3$, —$C_2H_5$, —$C_3H_7$ and the like. The same applies to other groups.

18

As used herein, the "halogen atom" means a fluorine atom, a chlorine atom, a bromine atom or an iodine atom.

19

As used herein, the "$C_{1-8}$ alkyl group" means a linear or branched saturated hydrocarbon group having 1 to 8 carbon atoms. Examples of the "$C_{1-8}$ alkyl group" include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl and the like. The preferred is a $C_{1-4}$ alkyl group.

20

As used herein, the "$C_{1-6}$ alkyl group" means a linear or branched saturated hydrocarbon group having 1 to 6 carbon atoms. Examples of the "$C_{1-6}$ alkyl group" include methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl and the like. The preferred is a $C_{1-4}$ alkyl group.

21

As used herein, the "$C_{1-4}$ alkyl group" means a linear or branched saturated hydrocarbon group having 1 to 4 carbon atoms. Examples of the "$C_{1-4}$ alkyl group" include methyl, ethyl, propyl, isopropyl, butyl, isobutyl, sec-butyl and tert-butyl.

22

As used herein, the "$C_{1-6}$ alkoxy group" means a group represented by the formula $R^{11}O$— wherein $R^{11}$ is a $C_{1-6}$ alkyl group. Examples of the "$C_{1-6}$ alkoxy group" include methoxy, ethoxy, propoxy, isopropoxy, butyloxy, isobutyloxy, sec-butyloxy, tert-butyloxy, pentyloxy, hexyloxy and the like. The preferred is a $C_{1-4}$ alkoxy group.

23

As used herein, the "$C_{1-6}$ haloalkyl group" means a group in which the one or more hydrogen atoms of the "$C_{1-6}$ alkyl group" are replaced with halogen atoms. Examples of the "$C_{1-6}$ haloalkyl group" include fluoromethyl, 2-fluoroethyl, 3-fluoropropyl, 4-fluorobutyl, trifluoromethyl, difluoromethyl, perfluoroethyl, perfluoropropyl, chloromethyl, 2-chloroethyl, bromomethyl, 2-bromoethyl, iodomethyl, 2-iodoethyl and the like. The preferred is trifluoromethyl.

24

As used herein, the "$C_{1-6}$ haloalkoxy group" means a group in which the one or more hydrogen atoms of the "$C_{1-6}$ alkoxy group" are replaced with halogen atoms. Examples of the "$C_{1-6}$ haloalkoxy group" include bromomethoxy, 2-bromoethoxy, 3-bromopropoxy, 4-bromobutoxy, iodomethoxy, 2-iodoethoxy, 3-iodopropoxy, 4-iodobutoxy, fluoromethoxy, 2-fluoroethoxy, 3-fluoropropoxy, 4-fluorobutoxy, tribromomethoxy, trichloromethoxy, trifluoromethoxy, difluoromethoxy, perfluoroethoxy, perfluoropropoxy, perfluoroisopropoxy, 1,1,2,2-tetrafluoroethoxy and 2-chloro-1,1,2-trifluoroethoxy.

25

As used herein, the "$C_{1-6}$ alkylsulfanyl group" means a group represented by the formula $R^{11}S$— wherein $R^{11}$ is a $C_{1-6}$ alkyl group. Examples of the "$C_{1-6}$ alkylsulfanyl group" include methylsulfanyl, ethylsulfanyl, propylsulfanyl, isopropylsulfanyl, butylsulfanyl, isobutylsulfanyl, sec-butylsulfanyl, tert-butylsulfanyl, pentylsulfanyl, hexylsulfanyl and the like. The preferred is a $C_{1-4}$ sulfanyl group.

26

As used herein, the "mono-$C_{1-6}$ alkylamino group" means a group represented by the formula $R^{11}NH$— wherein $R^{11}$ is a $C_{1-6}$ alkyl group. Examples of the "mono-$C_{1-6}$ alkylamino group" include methylamino, ethylamino, propylamino, isopropylamino, butylamino, isobutylamino, sec-butylamino, tert-butylamino, pentylamino, hexylamino and the like. The preferred is a mono-$C_{1-4}$ alkylamino group.

27

As used herein, the "di-$C_{1-6}$ alkylamino group" means a group represented by the formula $R^{11}{}_2N$— wherein the two $R^{11}$ are each independently a $C_{1-6}$ alkyl group. Examples of the "di-$C_{1-6}$ alkylamino group" include dimethylamino, diethylamino, N-ethyl-N-methylamino, dipropylamino, diisopropylamino, dibutylamino, diisobutylamino, disec-butylamino, ditert-butylamino, dipentylamino, dihexylamino and the like. The preferred is a alkylamino group.

28

As used herein, the "$C_{1-6}$ alkoxy-carbonyl group" means a group represented by the formula $R^{11}O$ C(═O)— wherein $R^{11}$ is a $C_{1-6}$ alkyl group. Examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like. The preferred is a $C_{1-4}$ alkoxy-carbonyl group.

29

As used herein, the "$C_{3-8}$ cycloalkyl group" means a cyclic saturated hydrocarbon group having 3 to 8 carbon atoms. Examples of the "$C_{3-8}$ cycloalkyl group" include cyclopropyl, cyclobutyl, cyclopentyl, cyclohexyl, cycloheptyl and cyclooctyl.

30

As used herein, the "$C_{6-10}$ aryl group" means a hydrocarbon group having 6 to 10 carbon atoms and having aromaticity. Examples of the "$C_{6-10}$ aryl group" include phenyl, 1-naphthyl and 2-naphthyl. The preferred is phenyl.

31

As used herein, the "$C_{7-16}$ aralkyl group" means the "$C_{1-6}$ alkyl group" substituted by the "$C_{6-10}$ aryl group". Examples of the "$C_{7-16}$ aralkyl group" include benzyl, 1-phenylethyl, 2-phenylethyl, 3-phenylpropyl, 4-phenylbutyl, (1-naphthyl)methyl, (2-naphthyl)methyl and the like. The preferred is benzyl.

32

As used herein, the "$C_{6-10}$ arene" means a hydrocarbon ring having 6 to 10 carbon atoms and having aromaticity. Examples of the "$C_{6-10}$ arene" include benzene and naphthalene. The preferred is benzene.

As used herein, Examples of the substituent of the "optionally substituted $C_{6-10}$ arene" include a halogen atom, a cyano group, a $C_{1-6}$ alkyl group, a hydroxy group, a $C_{1-6}$ alkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

33

As used herein, the "nitrogen-containing heterocycle" include a ring containing at least one nitrogen atom, and optionally further containing hetero atom(s) selected from a nitrogen atom, an oxygen atom and a sulfur atom. Examples of the "nitrogen-containing heterocycle" include aziridine, azetidine, pyrrolidine, piperidine, piperazine, morpholine, thiomorpholine and the like. The preferred is a 3- to 8-membered nitrogen-containing heterocycle, and the more preferred is a 5- or 6-membered nitrogen-containing heterocycle.

34

Hereinafter, the production method of the present invention is explained.

In the present invention, aromatic heterocycle-substituted difluoroacetic acid derivative (III) is produced by reacting N-oxido aromatic heterocyclic compound (I) with tetrafluoroethylene, in the presence of compound (II), in a solvent selected from an aromatic hydrocarbon solvent, an ester solvent and an ether solvent. The reaction mechanism is as follows.

35

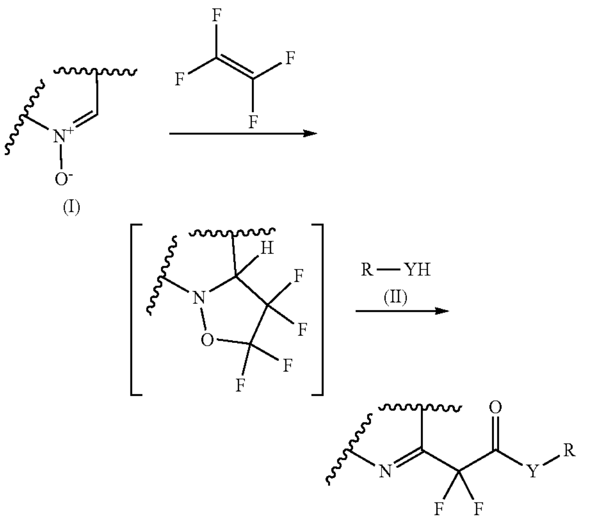

(I)

(III)

36

Specific examples of N-oxido aromatic heterocyclic compound (I) include the following N-oxido aromatic heterocyclic compounds (IA) and (IB):

37

(IA)

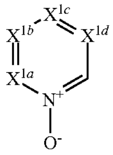

(IB)

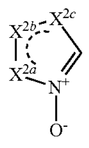

38 wherein $X^{1a}$ is $CR^{1a}$ or N;

$X^{1b}$ is $CR^{1c}$ or N;

$X^{1c}$ is $CR^{1c}$ or N;

$X^{1d}$ is $CR^{1d}$ or N;

$R^{1a}$, $R^{1b}$, $R^{1c}$ and $R^{1d}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{1a}$ and $R^{1b}$, $R^{1b}$ and $R^{1c}$, or $R^{1c}$ and $R^{1d}$ are optionally taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group;

$X^{2a}$ is $CR^{2a}$, N, $NR^{2a}$, S or O;

$X^{2b}$ is $CR^{2b}$ or N;

$X^{2c}$ is $OR^{2c}$, N, $NR^{2c}$, S or O; and $R^{2a}$, $R^{2b}$ and $R^{2c}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{2a}$ and $R^{2b}$, or $R^{2b}$ and $R^{2c}$ are optionally taken together to form a $C_{6-10}$ arene optionally substituted by substituent(s) selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

$R^{1b}$, $R^{1c}$ and $R^{1d}$ are preferably each independently a hydrogen atom, a cyano group or a $C_{1-6}$ alkyl group, or $R^{1a}$ and $R^{1b}$, $R^{1b}$ and $R^{1c}$, or $R^{1c}$ and $R^{1d}$ are optionally taken together to form a $C_{6-10}$ arene optionally substituted by $C_{1-6}$ alkoxy-carbonyl group(s).

$R^{2a}$, $R^{2b}$ and $R^{2c}$ are preferably each independently a hydrogen atom, a $C_{1-6}$ alkyl group or a $C_{7-16}$ aralkyl group, or $R^{2a}$ and $R^{2b}$, or $R^{2b}$ and $R^{2c}$ are optionally taken together to form a $C_{6-10}$ arene.

39

In the formula (IB), one of the bond $R^{2a}$-$R^{2b}$ and the bond $R^{2b}$-$R^{2c}$ is a single bond, and the other is a double bond. Provided that when $X^{2a}$ is S or O, then the bond $R^{2a}$-$R^{2b}$ is a single bond, and the bond $R^{2b}$-$R^{2c}$ is a double bond. Also, provided that when $X^{2c}$ is S or O, then the bond $R^{2a}$-$R^{2b}$ is a double bond, and the bond $R^{2b}$-$R^{2}c$ is a single bond.

40

Specific examples of N-oxido aromatic heterocyclic compound (IA) include the following N-oxido aromatic heterocyclic compounds (IA-a)-(IA-e).

41
(IA-a)
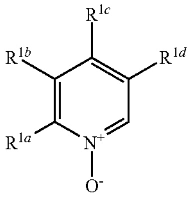
(IA-b)
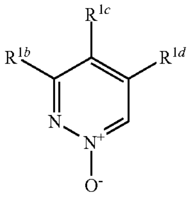
(IA-c)
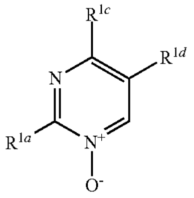
(IA-d)
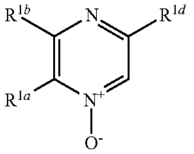
(IA-e)
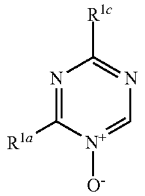
42
wherein each symbol in the formula is as defined above.
Among them, the preferred are (IA-a), (IA-b) and (IA-d).
Preferable specific examples of N-oxido aromatic heterocyclic compound (IA) include the following compounds.
43
(IA-a1)
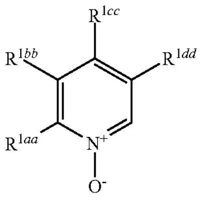
-continued
(IA-a2)
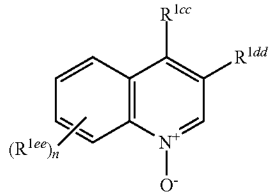
(IA-a3)
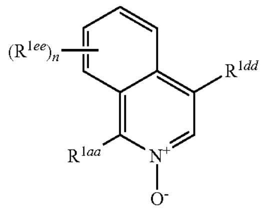
(IA-a4)
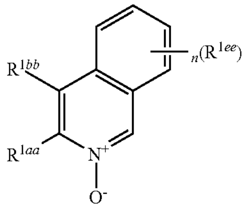
(IA-b1)
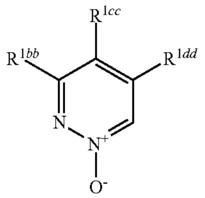
(IA-b2)
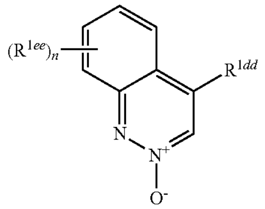
(IA-b3)
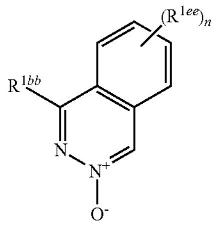
(IA-d1)
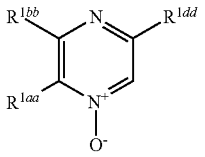

-continued (IA-d2)

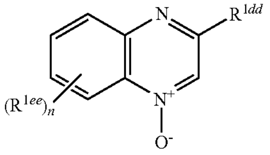

44 wherein $R^{1aa}$, $R^{1bb}$, $R^{1cc}$ and $R^{1dd}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group;

$R^{1ee}$ in the number of n are each independently a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group; and n is an integer of 0 to 4.

$R^{1aa}$, $R^{1bb}$, $R^{1cc}$ and $R^{1dd}$ are preferably each independently a hydrogen atom, a cyano group or a $C_{1-6}$ alkyl group;

$R^{1ee}$ in the number of n are preferably each independently a $C_{1-6}$ alkoxy-carbonyl group; and n is 0 or 1.

45

Specific examples of N-oxido aromatic heterocyclic compound (IB) include the following N-oxido aromatic heterocyclic compounds (IB-a)-(IB-ff).

46

(IB-a)

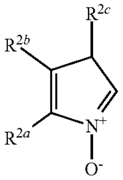

(IB-b)

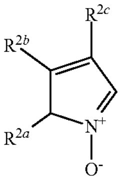

(IB-c)

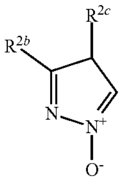

-continued (IB-d)

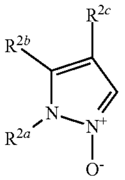

(IB-e)

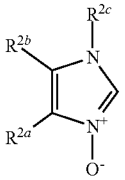

(IB-f)

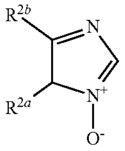

(IB-g)

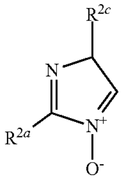

(IB-h)

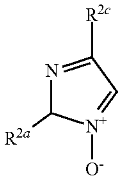

(IB-i)

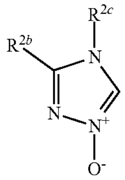

(IB-j)

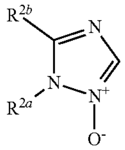

(IB-k)

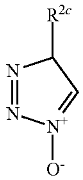

-continued
(IB-l)
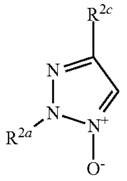
(IB-m)
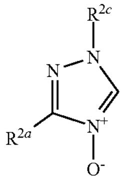
(IB-n)
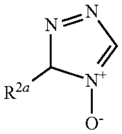
(IB-o)
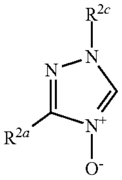
(IB-p)
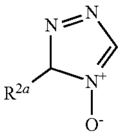
(IB-q)
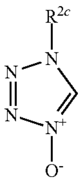
(IB-r)
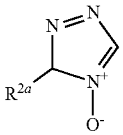
(IB-s)
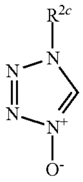
(IB-t)
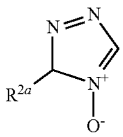
-continued
(IB-u)
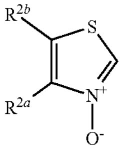
(IB-v)
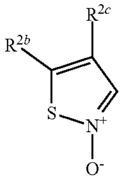
(IB-w)
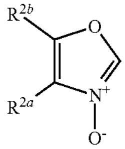
(IB-x)
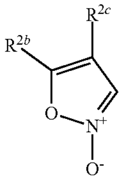
(IB-y)
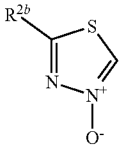
(IB-z)
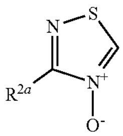
(IB-aa)
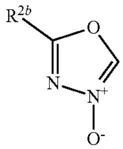
(IB-bb)
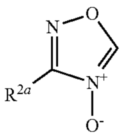
(IB-cc)
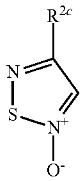

-continued (IB-dd)

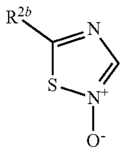

(IB-ee)

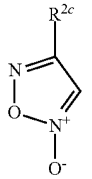

(IB-ff)

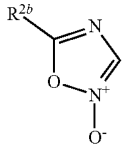

47

48 wherein each symbol in the formula is as defined above.

Among them, the preferred are (IB-e), (IB-u) and (IB-w).

Preferable specific examples of N-oxido aromatic heterocyclic compound (IB) include the following compounds.

49

(IB-e1)

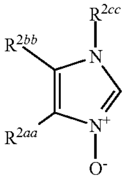

(IB-e2)

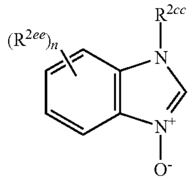

(IB-e3)

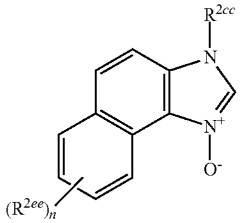

(IB-u1)

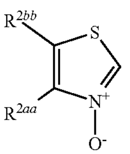

-continued (IB-u2)

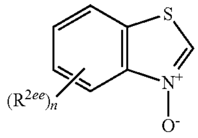

(IB-w1)

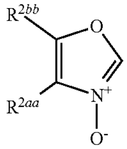

(IB-w2)

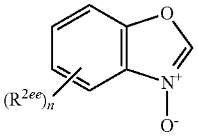

50 wherein $R^{2aa}$, $R^{2bb}$ and $R^{2cc}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group;

$R^{2ee}$ in the number of n are each independently a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group; and n is an integer of 0 to 4.

$R^{2aa}$, $R^{2bb}$ and $R^{2cc}$ are preferably each independently a hydrogen atom, a $C_{1-6}$ alkyl group or a $C_{7-16}$ aralkyl group; and n is 0.

51

N-Oxido aromatic heterocyclic compound (I) may be commercially available, or can be produced according to a method known per se.

52

Tetrafluoroethylene ($CF_2{=}CF_2$) can be produced according to a known method. Since tetrafluoroethylene is in a gaseous state at room temperature under atmospheric pressure, it is added to the reaction system by inflow. In this case, tetrafluoroethylene diluted with nitrogen gas may be flowed into the reaction system. The amount of the tetrafluoroethylene to be used is generally 1 to 100 mol, preferably 1 to 10 mol, per 1 mol of N-oxido aromatic heterocyclic compound (I).

53

The reaction is carried out in the presence of compound (II). R in compound (II) is preferably a $C_{1-8}$ alkyl group optionally substituted by substituent(s) selected from a halogen atom, a cyano group, a $C_{1-6}$ alkoxy group and a $C_{1-6}$ haloalkoxy group; a $C_{7-16}$ aralkyl group or a $C_{6-10}$ aryl group, which of each is optionally substituted by substituent (s) selected from a halogen atom, a cyano group, a $C_{1-6}$ alkyl group, a $C_{1-6}$ haloalkyl group, a $C_{1-6}$ alkoxy group and a $C_{1-6}$ haloalkoxy group, more preferably a $C_{1-6}$ alkyl group.

Y in compound (II) is preferably O or $NR^Y$, more preferably O.

$R^Y$ in compound (II) is preferably a hydrogen atom or a $C_{1-6}$ alkyl group, or $R^Y$ and R are taken together to form a 5- or 6-membered nitrogen-containing heterocycle (e.g., morpholine) with the nitrogen atom to which they are bond.

Preferable specific examples of compound (II) include butanol, morpholine and the like.

The amount of compound (II) to be used can be appropriately selected, and is preferably 0.05 to 0.5 times the volume of the solvent described below.

54

The reaction may be carried out in the presence of an additive.

55

The reaction is carried out in a solvent selected from an aromatic hydrocarbon solvent, an ester solvent and an ether solvent. The use of such solvent allows for good dissolution of tetrafluoroethylene and thus the production of aromatic heterocycle-substituted difluoroacetic acid derivative (III) with few by-products.

Examples of the aromatic hydrocarbon solvent include toluene, xylene, nitrobenzene and the like.

Examples of the ester solvent include butyl acetate, octyl acetate and the like.

Examples of the ether solvent include dibutyl ether, cyclopentyl methyl ether and the like.

The solvent used in the reaction is preferably a solvent having a boiling point of 80° C. or higher, more preferably a solvent having a boiling point of 100° C. or higher, particularly preferably a solvent having a boiling point of 110° C. or higher, from the aspect of the reaction temperature. Examples of such solvents include toluene, xylene, nitrobenzene, butyl acetate, octyl acetate, dibutyl ether, cyclopentyl methyl ether and the like. Among them, the preferred are toluene and butyl acetate.

The amount of the solvent to be used is generally 100 to 1000 times, preferably 100 to 200 times the volume of N-oxido aromatic heterocyclic compound (I).

56

The reaction may be carried out in a flow system while flowing tetrafluoroethylene into a mixture of N-oxido aromatic heterocyclic compound (I), compound (II) and a solvent. Alternatively, the reaction may be carried out in a sealed system after flowing tetrafluoroethylene into a mixture of N-oxido aromatic heterocyclic compound (I), compound (II) and a solvent. The reaction is carried out preferably in a sealed system, more preferably under pressure in the range of 0.1 to 100.0 MPa, particularly preferably in the range of 0.1 to 10.0 MPa, from the aspect of the reaction efficiency and reduction of by-products.

When N-oxido aromatic heterocyclic compound (I) is represented by the formula (IA), and $R^{1a}$ and $R^{1b}$, $R^{1b}$ and $R^{1c}$, or $R^{1c}$ and $R^{1d}$ are taken together to form the above $C_{6-10}$ arene, then the reaction is carried out preferably under pressure in the range of 0.1 to 10.0 MPa, more preferably in the range of 0.1 to 1.0 MPa, particularly preferably in the range of 0.1 to 0.5 MPa, from the aspect of ease of the reaction progress and increase in the reaction rate.

On the other hand, when N-oxido aromatic heterocyclic compound (I) is represented by the formula (IA), and does not form the above $C_{6-10}$ arene, then the reaction may be carried out under pressure in the above range. From the aspect of ease of the reaction progress and increase in the reaction rate, the reaction may be carried out preferably under pressure in the range of 0.1 to 30.0 MPa, more preferably in the range of 1.5 to 3.0 MPa, particularly preferably in the range of 2.0 to 2.5 MPa.

Prior to the inflow of tetrafluoroethylene, the reaction system is preferably degassed in advance. The reaction is also carried out preferably under nitrogen atmosphere.

57

The reaction is carried out generally at 100° C. or higher, preferably at temperature in the range of 100 to 300° C.

When N-oxido aromatic heterocyclic compound (I) is represented by the formula (IA), and $R^{1a}$ and $R^{1b}$, $R^{1b}$ and $R^{1c}$, or $R^{1c}$ and $R^{id}$ are taken together to form the above $C_{6-10}$ arene, then the reaction is carried out preferably at temperature in the range of 100 to 200° C., particularly preferably in the range of 100 to 150° C., from the aspect of ease of the reaction progress and increase in the reaction rate.

On the other hand, when N-oxido aromatic heterocyclic compound (I) is represented by the formula (IA), and does not form the above $C_{6-10}$ arene, then the reaction may be carried out at temperature in the above range. From the aspect of ease of the reaction progress and increase in the reaction rate, the reaction may be carried out preferably at temperature in the range of 200 to 300° C., particularly preferably in the range of 200 to 250° C.

The reaction time varies depending on the kinds of N-oxido aromatic heterocyclic compound (I) and compound (II), and the reaction temperature, and it is generally 12 to 120 hr, preferably 24 to 48 hr.

58

After the completion of the reaction, the objective aromatic heterocycle-substituted difluoroacetic acid derivative (III) can be isolated and purified from the reaction mixture according to conventional method, for example, a separation means such as concentration, crystallization, recrystallization, distillation, solvent extraction, fractional distillation, column chromatography and the like.

59

The container used for the reaction of tetrafluoroethylene and N-oxido aromatic heterocyclic compound (I) is not limited as long as it does not adversely affect the reaction. For example, metal containers and the like can be used. Since olefin in a gaseous state under the reaction condition is handled in the present invention, the use of air-sealing, pressure-resistant containers is preferable. Moreover, since the compound generated as the reaction progresses may become a reaction inhibitor by reacting with the metal of the reaction container, the use of containers lined with resin such as PFA or glass is preferable.

60

For aromatic heterocycle-substituted difluoroacetic acid derivative (III) thus obtained, for example, aromatic heterocycle-substituted difluoroacetic acid derivative (III) wherein Y is O can be led to a difluoromethyl-substituted aromatic heterocyclic compound having a partial structure represented by the formula (IV):

61

(IV)

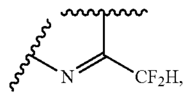

62 which is useful as a synthetic intermediate for pharmaceutical or agrochemical products, by a known method, for example, hydrolysis, followed by decarboxylation.

EXAMPLES

63

The present invention is explained in detail in the following by referring to Examples, which are not to be construed as limitative.

[Analysis Method]

The present invention is explained in detail in the following by referring to Examples, which are not to be construed as limitative. Nuclear magnetic resonance spectrum (NMR) was measured using JNM-AL300 manufactured by JEOL Ltd. $^1$H NMR was measured at 300 MHz using tetramethylsilane as standard.

Mass spectrometry (LC-MS) was measured using liquid chromatograph mass spectrum system (LCMS6120B) manufactured by Agilent Technologies. Mass spectrometry (GC-MS) was determined by electron ionization (EI) using gas chromatograph mass spectrometer (GCMS-QP5000V2 or GCMS-QP2010Ultra) manufactured by Shimadzu Corporation.

64

Example 1

65

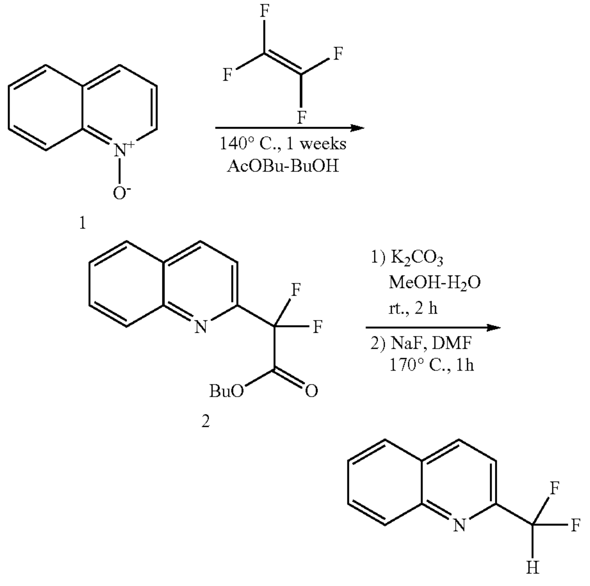

1

2

3

66

A SUS reactor having a volume of 25 cm$^3$ was charged with butyl acetate (10 ml) and 1-butanol (1 ml), and the mixture was stirred, and kept at 25° C. Then, quinoline N-oxide (109 mg, 0.751 mmol, Compound 1) was added thereto, and the mixture was degassed under reduced pressure. Tetrafluoroethylene diluted to 50% with nitrogen gas was refilled until the reactor pressure reached 0.1 MPa, and the mixture was kept stirred under heating at 140° C. for one week. By measuring $^1$H-NMR and LC-MS of the crude solution after the completion of the reaction, it was found that Compound 2 was obtained in a yield of 89%.

The reaction solution was concentrated as it is. Compound 2 (20 mg, 0.0677 mmol) was dissolved in methanol (0.2 ml), 1N aqueous potassium carbonate solution (0.2 ml)

was added thereto, and the mixture was stirred, and kept stirred at 25° C. for 18 hr. Then, 5% aqueous hydrochloric acid solution (1 ml) was added thereto, and the mixture was extracted with ethyl acetate. The organic layer was separated, and washed with saturated brine. The organic layer was concentrated, and the obtained crude product was dissolved in N,N-dimethylformaldehyde (1 ml). Sodium fluoride (23 mg) was added thereto, and the mixture was kept stirred under heating at 170° C. for 1 hr. By measuring $^1$H-NMR and GC-MS of the crude solution after the completion of the reaction, it was found that Compound 3 was obtained in a yield of 92%.

$^1$H-NMR and LC-MS of the above Compound (2) are shown below.

$^1$H-NMR ($CDCl_3$) δ 8.35 (d, 1H), 8.15 (d, 1H), 7.89 (d, 1H), 7.72-7.81 (m, 2H), 7.63 (t, 1H), 4.36 (t, 2H), 1.67 (tt, 2H), 1.35 (tt, 2H), 0.88 (t, 3H)

LC-MS: [M+1]=280

$^1$H-NMR and GC-MS of the above Compound (3) are shown below.

$^1$H-NMR ($CDCl_3$) δ 8.34 (d, 1H), 8.15 (d, 1H), 7.90 (d, 1H), 7.80 (dd, 1H), 7.74 (d, 1H), 7.65 (dd, 1H), 6.79 (t, 1H)

GC-MS (EI): [M+]=179

67

Reference Example 1

68

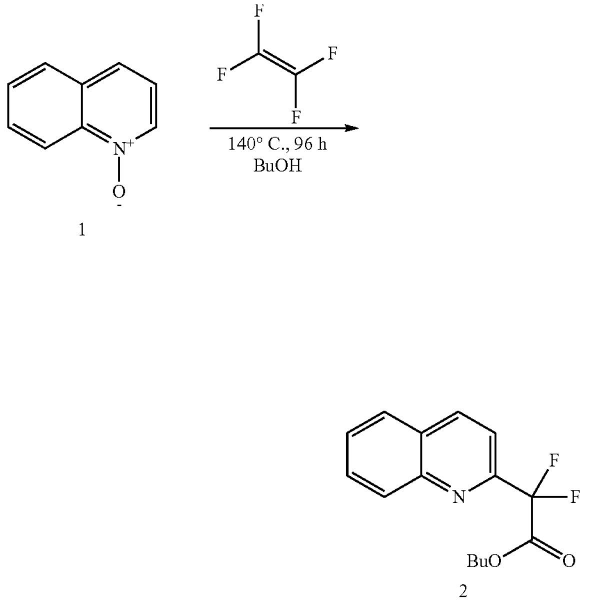

1

2

A crude solution containing Compounds 2 and 3 was obtained from Compound 1 in the same procedure as in Example 1, except that butyl acetate were not used. By measuring $^1$H-NMR and GC-MS of the crude solution after the completion of the reaction, it was found that Compound 2 was obtained in a yield of 13%.

69

Example 2

70

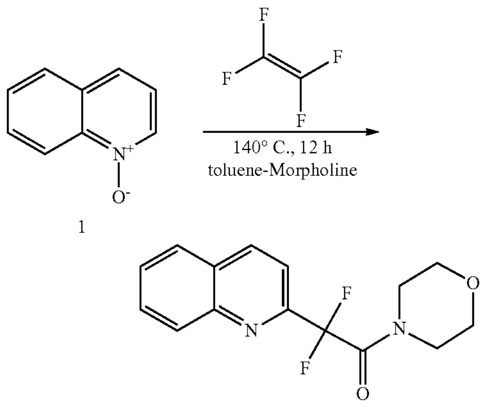

1

4

71

A SUS reactor having a volume of 25 $cm^3$ was charged with toluene (7 ml) and morpholine (0.3 ml), and the mixture was stirred, and kept at 25° C. Then, quinoline N-oxide (109 mg, 0.751 mmol, Compound 1) was added thereto, and the mixture was degassed under reduced pressure. Tetrafluoroethylene diluted to 50% with nitrogen gas was refilled until the reactor pressure reached 0.1 MPa, and the mixture was kept stirred under heating at 140° C. for 12 hr. By measuring $^1$H-NMR and LC-MS of the crude solution after the completion of the reaction, it was found that Compound 4 was obtained in a yield of 37%.

$^1$H-NMR and LC-MS of the above Compound (4) are shown below.

$^1$H-NMR ($CDCl_3$) δ 8.33 (d, 1H), 8.11 (d, 1H), 7.88 (d, 1H), 7.82-7.74 (m, 2H), 7.63 (t, 1H), 3.76 (s, 4H), 3.64 (t, 2H), 3.57 (t, 2H).

LC-MS: [M+1]=293

72

Example 3

73

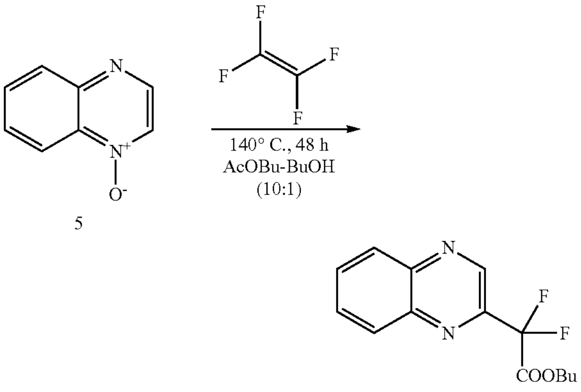

5

6

74

A crude solution containing Compound 6 was obtained from Compound 5 in the same procedure as in Example 1. By measuring $^1$H-NMR and LC-MS of the crude solution after the completion of the reaction, it was found that Compound 6 was obtained in a yield of 61%.

$^1$H-NMR and LC-MS of the above Compound (6) are shown below.

$^1$H-NMR ($CDCl_3$) δ 9.23 (s, 1H), 8.10-8.22 (m, 2H), 7.80-7.92 (m, 2H), 4.36 (t, 2H), 1.70 (tt, 2H), 1.38 (tt, 2H), 0.92 (t, 3H) LC-MS: [M+1]=281

75

Example 4

76

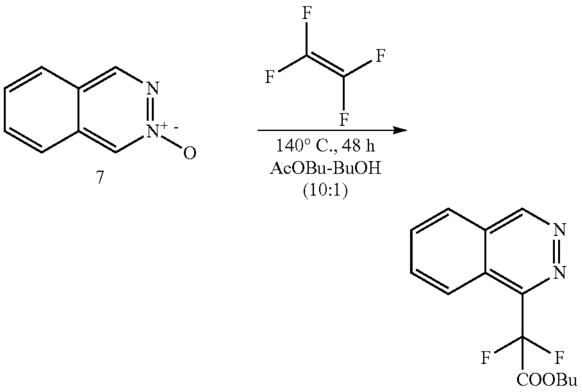

7

8

77

A crude solution containing Compound 8 was obtained from Compound 7 in the same procedure as in Example 1. By measuring $^1$H-NMR and LC-MS of the crude solution after the completion of the reaction, it was found that Compound 8 was obtained in a yield of 41%.

$^1$H-NMR and LC-MS of the above Compound (8) are shown below. $^1$H-NMR ($CDCl_3$) δ9.58 (1H, s), 8.46 (1H, m), 7.77-8.09 (3H, m), 4.48 (2H, t), 1.73 (2H, tt), 1.44 (2H, tt), 0.95 (3H, t).

LC-MS: [M+1]=281

78

Example 5

79

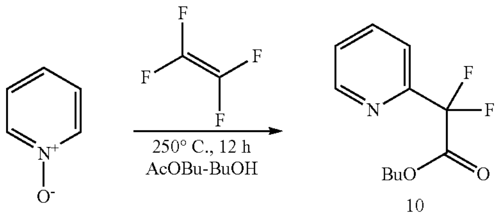

9

10

80

A PFA-lined SUS reactor having a volume of 300 $cm^3$ was charged with butyl acetate (30 ml) and butanol (3 ml), and the mixture was stirred, and kept at 25° C. Then, pyridine N-oxide (336.4 mg, 3.54 mmol, Compound 9) was added thereto, and the mixture was degassed under freezing. Tetrafluoroethylene diluted to 50% with nitrogen gas was refilled until the reactor pressure reached 0.3 MPa, and the mixture was kept stirred under heating at 250° C. for 8 hr. By measuring $^1$H-NMR and LC-MS of the crude solution after the completion of the reaction, it was found that Compound 10 was obtained in a yield of 28%.

$^1$H-NMR and LC-MS of the above Compound (10) are shown below.

$^1$H-NMR (ACETN) δ8.69 (d, 1H), 8.08 (ddd, 1H), 7.84 (ddd, 1H), 7.60-7.63 (m, 1H), 4.33 (t, 2H), 1.65 (tt, 2H), 1.35 (tt, 2H), 0.89 (t, 3H)

LC-MS: [M+1]=230

81

Example 6

82

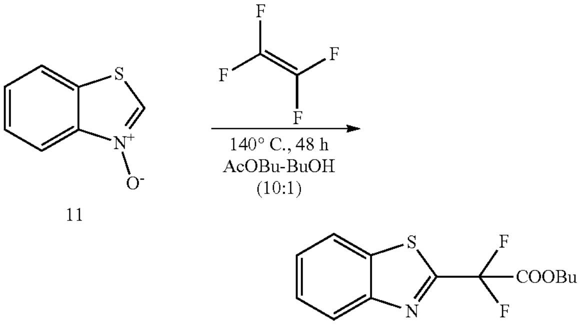

11

12

83

A crude solution containing Compound 12 was obtained from Compound 11 in the same procedure as in Example 1. By measuring $^1$H-NMR and LC-MS of the crude solution after the completion of the reaction, it was found that Compound 12 was obtained in a yield of 42%.

$^1$H-NMR and LC-MS of the above Compound (12) are shown below.

$^1$H-NMR ($CDCl_3$) δ8.15 (1H, d), 7.97 (1H, d), 7.54 (2H, dt), 4.44 (2H, t), 1.59 (2H, tt), 1.34 (2H, tt), 0.94 (3H, t).

LC-MS: [M+1]=286

84

Example 7

85

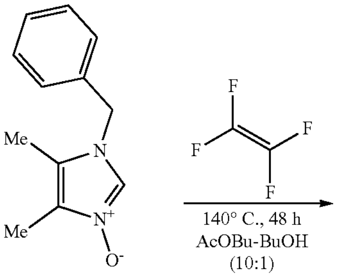

13

-continued

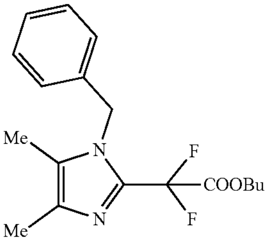

14

86

A crude solution containing Compound 14 was obtained from Compound 13 in the same procedure as in Example 1. By measuring $^1$H-NMR and LC-MS of the crude solution after the completion of the reaction, it was found that Compound 14 was obtained in a yield of 55%.

$^1$H-NMR and LC-MS of the above Compound (14) are shown below.

$^1$H-NMR ($CDCl_3$) δ 7.31-7.36 (m, 2H), 7.09 (dd, 2H), 4.81 (s, 2H), 4.35 (t, 2H), 2.10 (s, 3H), 1.97 (s, 3H), 1.72 (tt, 2H), 1.41 (tt, 2H), 0.93 (t, 3H)

LC-MS: [M+1]=337

87

Example 8

88

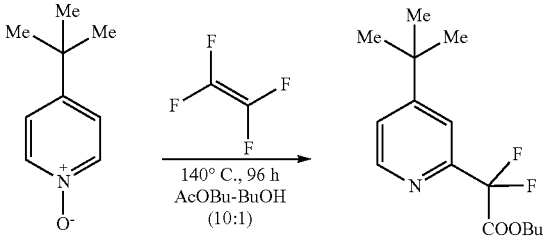

15

16

89

A crude solution containing Compound 16 was obtained from Compound 15 in the same procedure as in Example 1. By measuring $^1$H-NMR and GC-MS of the crude solution after the completion of the reaction, it was found that Compound 16 was obtained in a yield of 25%.

$^1$H-NMR and GC-MS of the above Compound (16) are shown below.

$^1$H-NMR ($CDCl_3$) δ 8.50 (d, 1H), 7.72 (d, 1H), 7.09 (s, 1H), 3.90 (t, 2H), 1.59 (tq, 2H), 1.35 (s, 9H), 1.34 (m, 2H), 0.94 (t, 3H)

GC-MS (EI): [M+]=285

90

Example 9

91

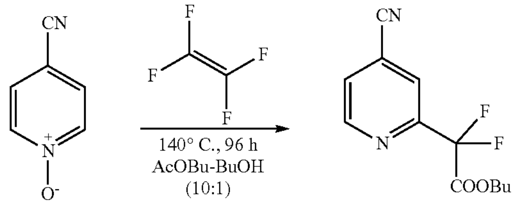

17 18

92

A crude solution containing Compound 18 was obtained from Compound 17 in the same procedure as in Example 1. By measuring $^1$H-NMR and GC-MS of the crude solution after the completion of the reaction, it was found that Compound 18 was obtained in a yield of 26%.

$^1$H-NMR and GC-MS of the above Compound (18) are shown below.

$^1$H-NMR ($CDCl_3$) δ 8.95 (d, 1H), 8.02 (s, 1H), 7.60 (d, 1H), 3.90 (t, 2H), 1.59 (d, 2H), 1.34 (tq, 2H), 0.94 (t, 3H), GC-MS (EI): [M+]=254

INDUSTRIAL APPLICABILITY

93

According to the present invention, by an easy and inexpensive method of flowing tetrafluoroethylene into N-oxido aromatic heterocyclic compound (I) in the presence of compound (II) in a specific solvent, aromatic heterocycle-substituted difluoroacetic acid derivative (III) with few by-products can be produced in one step.

94

This application is based on patent application No. 2020-019211 filed on Feb. 6, 2020 in Japan, the contents of which are encompassed in full herein.

The invention claimed is:

1. A method for producing a compound having a partial structure represented by formula (III) (IIIA) or formula (IIIB):

(IIIA)

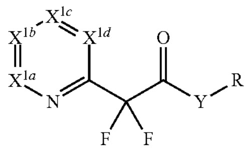

(IIIB)

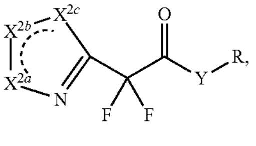

wherein R is a $C_{1-8}$ alkyl group, a $C_{3-8}$ cycloalkyl group, a $C_{7-16}$ aralkyl group or a $C_{6-10}$ aryl group, wherein the $C_{1-8}$ alkyl group is optionally substituted with at least one substituent selected from a halogen atom, a cyano group, a $C_{1-6}$ alkoxy group and a $C_{1-6}$ haloalkoxy group, and the $C_{3-8}$ cycloalkyl group, $C_{7-16}$ aralkyl group and $C_{6-10}$ aryl group are each optionally substituted with at least one substituent selected from a halogen atom, a cyano group, a $C_{1-6}$ alkyl group, a $C_{1-6}$ haloalkyl group, a $C_{1-6}$ alkoxy group and a $C_{1-6}$ haloalkoxy group, Y is O, S or $NR^Y$, and $R^Y$ is a hydrogen atom or a $C_{1-8}$ alkyl group, or $R^Y$ and R are optionally taken together to form a nitrogen-containing heterocycle with a nitrogen atom to which they are bonded, the method comprising:

reacting a compound of formula (IA) or (IB):

(IA)

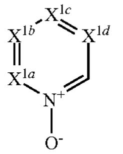

(IB)

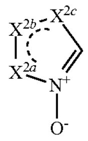

with tetrafluoroethylene, in the presence of a compound represented by the formula (II): R—YH in a solvent selected from an aromatic hydrocarbon solvent, an ester solvent and an ether solvent, wherein $X^{1a}$ is $CR^{1a}$ or N; $X^{1b}$ is $CR^{1b}$ or N; $X^{1c}$ is $CR^{1c}$ or N; $X^{1d}$ is $CR^{1d}$ or N;

$R^{1a}$, $R^{1b}$, $R^{1c}$ and $R^{1d}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{1a}$ and $R^{1b}$, $R^{1b}$ and $R^{1c}$, or $R^{1c}$ and $R^{1d}$ are optionally taken together to form a $C_{6-10}$ arene optionally substituted with at least one substituent selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group;

$X^{2a}$ is $CR^{2a}$, N, $NR^{2a}$, S or O; $X^{2b}$ is $CR^{2b}$ or N; $X^{2c}$ is $CR^{2c}$, N, $NR^{2c}$, S or O; and $R^{2a}$, $R^{2b}$ and $R^{2c}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group, or $R^{2a}$ and $R^{2b}$, or $R^{2b}$ and $R^{2c}$ are optionally taken together to form a $C_{6-10}$ arene optionally substituted with at least one substituent selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

2. The method according to claim 1, wherein the reaction is carried out at a temperature in the range of 100 to 300° C.

3. The method according to claim 1, wherein the reaction is carried out under a pressure in the range of 0.1 to 10.0 MPa.

4. The method according to claim 1, wherein the compound of formula (IA) is reacted, and $R^{1a}$ and $R^{1b}$, $R^{1b}$ and $R^{1c}$, or $R^{1c}$ and $R^{1d}$ in the formula are taken together to form a $C_{6-10}$ arene optionally substituted with at least one substituent selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

5. The method according to claim 1, wherein the compound of formula (IA) is reacted, and $R^{1a}$, $R^{1b}$, $R^{1c}$ and $R^{1d}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group.

6. The method according to claim 1, wherein the compound of formula (IB) is reacted, and $R^{2a}$ and $R^{2b}$, or $R^{2b}$ and $R^{2c}$ are taken together to form a $C_{6-10}$ arene optionally substituted with at least one substituent selected from a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group and a $C_{7-16}$ aralkyl group.

7. The method according to claim 1, wherein the compound of formula (IB) is reacted, and $R^{2a}$, $R^{2b}$ and $R^{2c}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group.

8. The method according to claim 1, wherein the compound of formula (IA) is reacted and comprises at least one selected from the group consisting of the following formulae (IA-a)-(IA-e):

(IA-a)

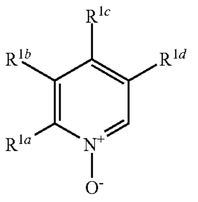

-continued (IA-b)

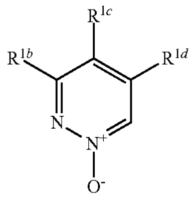

(IA-c)

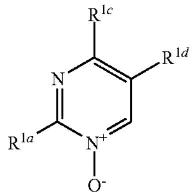

(IA-d)

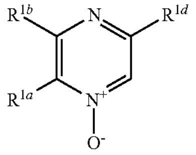

(IA-e)

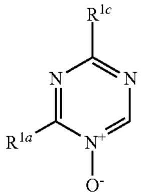

9. The method according to claim 1, wherein the compound of formula (IA) is reacted and comprises at least one selected from the group consisting of the following compounds of formulae (IA-a1)-(IA-d2):

(IA-a1)

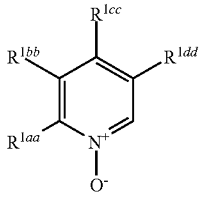

(IA-a2)

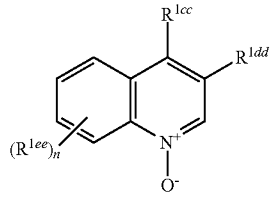

(IA-a3)

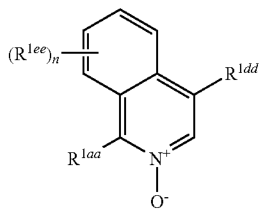

-continued (IA-a4)

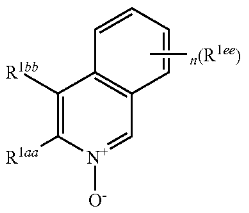

(IA-b1)

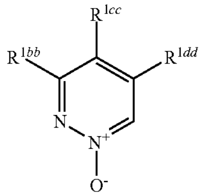

(IA-b2)

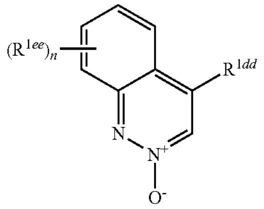

(IA-b3)

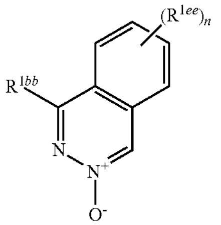

(IA-d1)

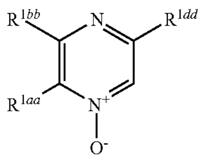

(IA-d2)

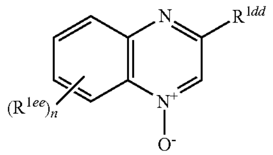

wherein $R^{1aa}$, $R^{1bb}$, $R^{1cc}$ and $R^{1dd}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group;

$R^{1ee}$ in the number of n are each independently a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group;

n is an integer of 0 to 4;

$R^{1aa}$, $R^{1bb}$, $R^{1cc}$ and $R^{1dd}$ are each independently a hydrogen atom, a cyano group or a $C_{1-6}$ alkyl group;

$R^{1ee}$ are each independently a $C_{1-6}$ alkoxy-carbonyl group; and n is 0 or 1.

10. The method according to claim 1, wherein the compound of formula (IB) is reacted and comprises at least one selected from the group consisting of the following formulae (IB-a)-(IB-ff):

(IB-a)

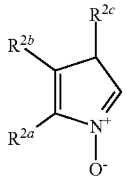

(IB-b)

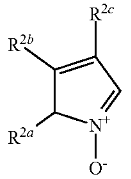

(IB-c)

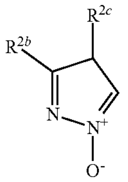

(IB-d)

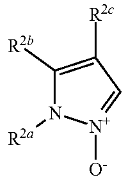

(IB-e)

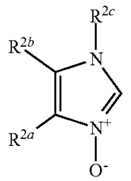

(IB-f)

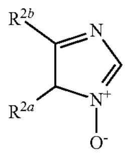

-continued
(IB-g)
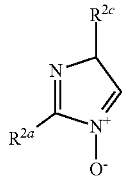
(IB-h)
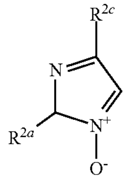
(IB-i)
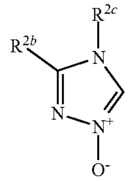
(IB-j)
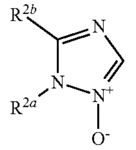
(IB-k)
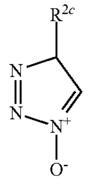
(IB-l)
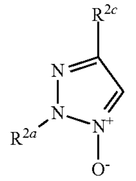
(IB-m)
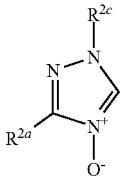
(IB-n)
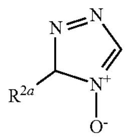
(IB-o)
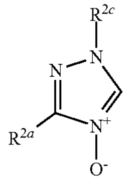
-continued
(IB-p)
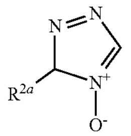
(IB-q)
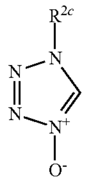
(IB-r)
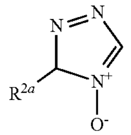
(IB-s)
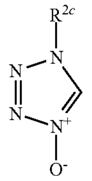
(IB-t)
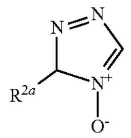
(IB-u)
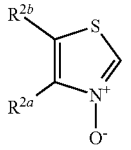
(IB-v)
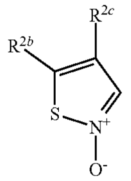
(IB-w)
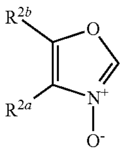
(IB-x)
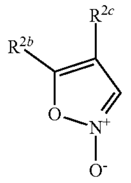

-continued (IB-y)

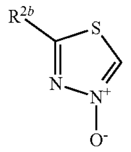

(IB-z)

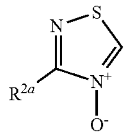

(IB-aa)

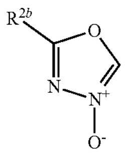

(IB-bb)

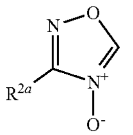

(IB-cc)

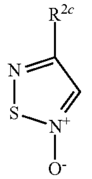

(IB-dd)

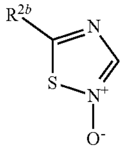

(IB-ee)

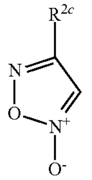

(IB-ff)

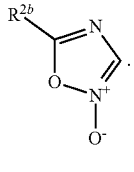

11. The method according to claim 1, wherein the compound of formula (IB) is reacted and comprises at least one selected from the group consisting of the following formulae (IB-e1)-(IB-w2):

(IB-e1)

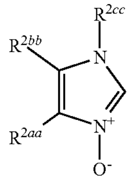

(IB-e2)

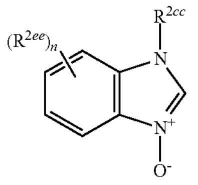

(IB-e3)

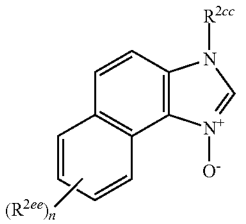

(IB-u1)

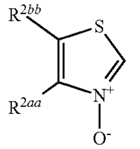

(IB-u2)

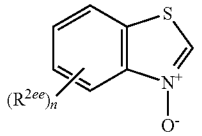

(IB-w1)

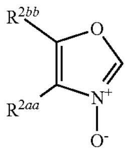

(IB-w2)

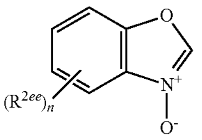

wherein $R^{2aa}$, $R^{2bb}$ and $R^{2cc}$ are each independently a hydrogen atom, a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxycarbonyl group, a $C_{6-10}$ aryl group or a $C_{7-16}$ aralkyl group;

$R^{2ee}$ are each independently a halogen atom, a cyano group, a $C_{1-6}$ alkyl group, a $C_{1-6}$ haloalkyl group, a hydroxy group, a $C_{1-6}$ alkoxy group, a $C_{1-6}$ haloalkoxy group, a sulfanyl group, a $C_{1-6}$ alkylsulfanyl group, an amino group, a mono-$C_{1-6}$ alkylamino group, a di-$C_{1-6}$ alkylamino group, a formyl group, a carboxy group, a $C_{1-6}$ alkoxy-carbonyl group, a $C_{6-10}$ aryl group or a $C_{7-16}$ aralkyl group;

n is an integer of 0 to 4;

$R^{2aa}$, $R^{2bb}$ and $R^{2cc}$ are preferably each independently a hydrogen atom, a $C_{1-6}$ alkyl group or a $C_{7-16}$ aralkyl group; and n is 0.

12. The method according to claim 1, wherein the tetrafluoroethylene is reacted in an amount between 1 to 100 mol per 1 mol of the compound of formula (IA) or (IB).

13. The method according to claim 1, wherein the aromatic hydrocarbon solvent comprises at least one selected from the group consisting of toluene, xylene, and nitrobenzene.

14. The method according to claim 1, wherein the solvent comprises at least one ester solvent selected from the group consisting of butyl acetate and octyl acetate.

15. The method according to claim 1, wherein the solvent comprises at least one ester solvent selected from the group consisting of dibutyl ether and cyclopentyl methyl ether.

16. The method according to claim 8, wherein the compound of formula (IA) comprises at least one compound selected from the group consisting of a compound of formula (5) and a compound of formula (7),

6

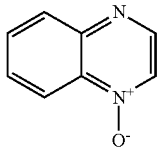

7

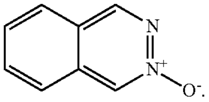

17. The method according to claim 9, wherein the compound of formula (IA) comprises at least one compound selected from the group consisting of a compound of formula (IA-a1), a compound of formula (IA-a2), and a compound of formula (IA-d2).

18. The method according to claim 9, wherein the compound of formula (IA) comprises at least one compound selected from the group consisting of a compound of formula (1), a compound of formula (9), a compound of formula (15), a compound of formula (17),

1

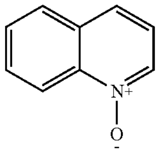

-continued

9

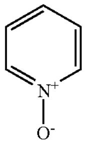

15

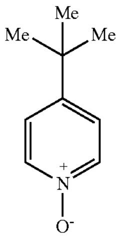

17

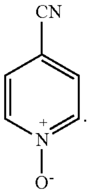

19. The method according to claim 10, wherein the compound of formula (IB) comprises at least one compound selected from the group consisting of a compound of formula (IB-e) and a compound of formula (IB-u).

20. The method according to claim 10, wherein the compound of formula (IB) comprises at least one compound selected from the group consisting of a compound of formula (11) and a compound of formula (13),

11

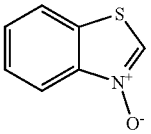

13

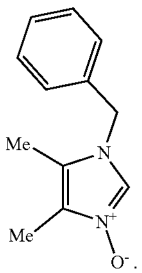

* * * * *